United States Patent
Schulman et al.

(10) Patent No.: US 6,934,572 B2
(45) Date of Patent: *Aug. 23, 2005

(54) IMPLANTABLE ENZYME-BASED MONITORING SYSTEM HAVING IMPROVED LONGEVITY DUE TO IMPROVED EXTERIOR SURFACES

(75) Inventors: Joseph H. Schulman, Santa Clarita, CA (US); Charles L. Byers, Canyon Country, CA (US); Gerald E. Adomian, Los Angeles, CA (US); Michael S. Colvin, Malibu, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 10/286,174

(22) Filed: Oct. 31, 2002

(65) Prior Publication Data

US 2003/0065254 A1 Apr. 3, 2003

Related U.S. Application Data

(60) Continuation of application No. 09/395,434, filed on Sep. 14, 1999, now Pat. No. 6,477,395, which is a division of application No. 08/954,166, filed on Oct. 20, 1997, now Pat. No. 6,119,028.

(51) Int. Cl.[7] ................................................ A61B 5/00
(52) U.S. Cl. ...................... 600/345; 600/347; 600/365; 204/415
(58) Field of Search ................................. 600/345–350, 600/365, 486, 488, 500, 505, 549, 561, 485; 204/415–419

(56) References Cited

U.S. PATENT DOCUMENTS

| 3,539,455 A | 11/1970 | Clark, Jr. ........................ 204/1 |
| 3,542,662 A | 11/1970 | Hicks et al. ................ 204/195 |

(Continued)

OTHER PUBLICATIONS

Gough, et al.; "Two–Dimensional Enzyme Electrode Sensor for Glucose", *Analytical Chemistry*, vol. 57, No. 12, pp. 2351–2357 (1985).

*Primary Examiner*—Robert L. Nasser
(74) *Attorney, Agent, or Firm*—Foley & Lardner LLP

(57) ABSTRACT

An implantable enzyme-based monitoring system suitable for long term in vivo use to measure the concentration of prescribed substances such as glucose is provided. In one embodiment, the implantable enzyme-based monitoring system includes at least one sensor assembly, an outer membrane surrounding the sensor assembly and having a window therein, and a polymeric window cover affixed to the outer membrane and covering the window. Preferably, the outer membrane of the monitoring system is silicone and the window cover is a polymer of 2-hydroxyethyl methacrylate (HEMA), N,N,-dimethylaminoethyl methacrylate (DMAEMA) and methacrylic acid (MA). Also provided herein is an implantable enzyme-based monitoring system having at least one sensor assembly, an outer membrane surrounding the sensor assembly and a coating affixed to the exterior surface of the outer membrane, wherein the coating resists blood coagulation and protein binding to the exterior surface of the outer membrane. Preferably, the coating is polyethylene glycol (PEG) and heparin in an 80:20 molar ratio. Finally, provided herein is a method of coating the exterior surface of the outer membrane of an implantable enzyme-based monitoring system comprising the steps of forming hydroxyl groups on the silicone surface by plasma etching; reacting the silicone surface with amino functionalized silane, thereby forming amino groups on the silicone surface; simultaneously, covalently binding polyethylene glycol (PEG) and heparin to the amino groups; and ionically binding heparin to the monitoring system surface.

13 Claims, 7 Drawing Sheets

U.S. PATENT DOCUMENTS

| | | |
|---|---|---|
| 4,252,123 A | 2/1981 | Kimmich .................... 128/635 |
| 4,431,004 A | 2/1984 | Bessman et al. ............ 128/635 |
| 4,484,987 A | 11/1984 | Gough ........................... 204/1 |
| 4,627,906 A | 12/1986 | Gough |
| 4,650,547 A | 3/1987 | Gough ........................... 204/1 |
| 4,671,288 A | 6/1987 | Gough ....................... 128/635 |
| 4,703,756 A | 11/1987 | Gough et al. ............... 123/635 |
| 4,759,828 A | 7/1988 | Young et al. ................... 204/1 |
| 4,781,798 A | 11/1988 | Gough ........................... 204/1 |
| 4,836,907 A | 6/1989 | Pedersen |
| 4,890,620 A | 1/1990 | Gough ....................... 128/635 |
| 5,007,424 A | 4/1991 | Ahsbahs et al. ............ 128/635 |
| 5,165,407 A | 11/1992 | Wilson et al. .............. 128/635 |
| 5,174,291 A | 12/1992 | Schoonen et al. .......... 128/632 |
| 5,190,041 A | 3/1993 | Palti ........................... 128/635 |
| 5,322,063 A | 6/1994 | Allen et al. .................. 128/635 |
| 5,330,634 A | 7/1994 | Wong et al. ................. 204/409 |
| 5,441,739 A | 8/1995 | Kossovsky et al. |
| 5,476,094 A | 12/1995 | Allen et al. |
| 5,497,772 A | 3/1996 | Schulman et al. .......... 128/635 |
| 5,571,166 A | 11/1996 | Dinh et al. |
| 5,660,163 A | 8/1997 | Schulman et al. |
| 5,694,932 A | 12/1997 | Michel ....................... 128/635 |
| 5,707,502 A | 1/1998 | McCaffrey et al. |
| 5,711,861 A | 1/1998 | Ward et al. ................. 204/403 |
| 5,791,344 A | 8/1998 | Schulman et al. |
| 5,999,848 A * | 12/1999 | Gord et al. .................... 607/2 |
| 6,259,937 B1 | 7/2001 | Schulman et al. .......... 600/345 |
| 6,477,395 B2 * | 11/2002 | Schulman et al. .......... 600/345 |

* cited by examiner

Derivatization of Heparin

Heparin (1 eqt.) + DDAB (4 eqt)

IN WATER (DDAB)

Heparin-Lipid Complex (Hep-L)

p-TsCl, Et₃N

Hep-L-OTs (one tosyl group per repeat unit of heparin)

Ionic binding of Heparin to the sensor surface

Assembled sensor after window filling

Incubate in a solution of heparin (Ph=6)

IMPLANTABLE ENZYME-BASED MONITORING SYSTEM HAVING IMPROVED LONGEVITY DUE TO IMPROVED EXTERIOR SURFACES

This application is a continuation of U.S. Ser. No. 09/395,434, filed Sep. 14, 1999, now U.S. Pat. No. 6,477,395, which application is a divisional of U.S. Ser. No. 08/954,166, filed Oct. 20, 1997, now U.S. Pat. No. 6,119,028.

BACKGROUND OF THE INVENTION

The present invention relates to implantable monitoring systems for the continuous in vivo measurement of biochemical substances, and more particularly to improved implantable enzyme-based glucose monitoring systems, small enough to be implanted through the lumen of a catheter or hypodermic needle, that measure the amount and rate of change of glucose in a patient's blood over an extended period of time.

Glucose is an important source of energy in the body and the sole source of energy for the brain. Glucose is stored in the body in the form of glycogen. In a healthy person, the concentration of glucose in the blood is maintained between 0.8 and 1.2 mg/ml by a variety of hormones, principally insulin and glucagon. If the blood-glucose concentration falls below this level neurological and other symptoms may result, such as hypoglycemia. Conversely, if the blood-glucose level is raised above its normal level, the condition of hyperglycemia develops, which is one of the symptoms of diabetes mellitus. The complications associated with both of these disorders, particularly if left uncorrected, can result in patient death. Thus, measuring and maintaining the concentration of glucose in the blood at a proper level is critically important for good health and longevity.

Unfortunately, some individuals are physically unable to maintain the proper level of glucose in their blood. For such individuals, the concentration of glucose in the blood can usually be altered, as required, to maintain health. For example, a shot of insulin can be administered to decrease the patient's blood glucose concentration, or conversely, glucose may be added to the blood, either directly, as through injection or administration of an intravenous (IV) solution, or indirectly, as through ingestion of certain foods or drinks.

Before a patient's glucose concentration can be properly adjusted, however, a determination must be made as to what the current blood glucose concentration is and whether that concentration is increasing or decreasing. Many implantable glucose monitoring systems have been described that are designed to provide continuous measurement of a patient's blood glucose concentration. See for example, U.S. Pat. Nos. 3,539,455; 3,542,662; 4,484,987; 4,650,547; 4,671,288; 4,703,756; 4,890,620; 5,165,407; and 5,190,041. Most of these systems are based on the "enzyme electrode" principle where an enzymatic reaction, involving glucose oxidase, is combined with an electrochemical sensor, to measure either oxygen or hydrogen peroxide, and used to determine the concentration of glucose in a patient's blood.

Generally, enzyme-based glucose monitoring systems, whether implantable or not, use glucose oxidase to convert glucose and oxygen to gluconic acid and hydrogen peroxide ($H_2O_2$). An electrochemical oxygen detector is then employed to measure the concentration of remaining oxygen after reaction of the glucose; thereby providing an inverse measurement of the blood glucose concentration. A second enzyme, catalase, is optionally included with the glucose oxidase to catalyze the decomposition of the hydrogen peroxide to water, in order to prevent interference in the measurements from the $H_2O_2$.

Thus, this system of measuring glucose requires that glucose be the limiting reagent of the enzymatic reaction. Where the system is to be used in vivo, this requirement can, and often does, pose a serious because, on a molar basis, the concentration of free oxygen in vivo is typically much less than that of glucose. This "oxygen deficit" prevents the exhaustion of glucose in the area of the enzymatic portion of the system and thus, results in an inaccurate determination of glucose concentration. Further, such an oxygen deficit can contribute to other performance related problems for the sensor assembly, including diminished sensor responsiveness and undesirable electrode sensitivity. See for example, the discussion in Gough et al., in *Two-Dimensional Enzyme Electrode Sensor for Glucose*, Vol 57 Analytical Chemistry pp 2351 et seq. (1985), incorporated by reference herein.

Attempts to solve the oxygen deficit problem, associated with in vivo glucose monitoring systems have previously been presented and are primarily based upon either reduction of the enzyme catalytic activity or regulation of the diffusion of glucose and oxygen through the use of specialized membranes. See for example, U.S. Pat. No. 4,484,987, Gough, D., hereby incorporated by reference, in its entirety. These solutions, however, have their own disadvantages. For example, reduction of the enzymatic activity of the monitoring system requires either a reduced concentration of enzyme or a thinner layer of active enzyme, both of which tend to shorten the useful life of the enzymatic sensor by reducing the amount of useful enzyme. Alternatively, a longer thinner layer of enzyme can be employed within the sensor assembly in order to locally reduce the enzymatic activity without loss of useful life to the sensor, but this tends to slow the responsiveness of the sensor and/or requires a larger (i.e. longer) sensor, which are both undesirable.

Use of specialized membranes to control the diffusion of glucose and oxygen into the sensor assembly, can also present problems. For example, as discussed in U.S. Pat. No. 5,322,063 issued to Allen et al. and incorporated by reference herein, in its entirety, controlling the diffusion of the glucose and oxygen through the use of specialized membranes can lead to slower responsiveness of the sensor and/or unintentional poisoning of the sensor and electrodes caused by migration of undesirable substances through the specialized membranes to the sensor. In particular, to the degree the specialized membrane comprises a hybrid of two different membrane types, having numerous junctions between two or more disparate membranes, concerns arise as to the integrity of such junctions, the appropriate ratio of the two membranes to one another and the appropriate configuration of the hybrid (i.e., for example, "islands" of one membrane type within and each surrounded by the other membrane type or alternating "stripes" of membrane types).

An additional concern that arises when a monitoring system is intended for use within the body of a patient, especially where it is to be used long term, relates to the biocompatibility of the system. The protective mechanisms of the body attempt to shield the body from the invasion of the monitoring system which is perceived as an unwanted foreign object. These protective mechanisms include, for example, encapsulation of the foreign object by the growth of isolating tissue and coagulation of blood on and around the foreign object. Obviously, encapsulation of and/or blood coagulation around all or part of the implantable sensor can significantly reduce or completely terminate the functionality of the device.

Often, the exterior surface of implantable monitoring systems are composed of silicone rubber, which is a reasonably biocompatable material. However, silicone rubber has been shown to induce thrombosis and encapsulation when compared to living endothelium. Many different approaches have been utilized to enhance the biocompatibility of silicone rubber and similar polymeric materials. However, presently, it is unclear exactly what the relationships of surface chemistry and morphology are to blood/body compatibility. This could be due to several factors. First, polymer surfaces often are not well characterized. Second, additives, processing aids and the like may have migrated to or may have been left behind at the polymer surface; thereby contributing to the unpredictable nature of the surface. Furthermore, even if the polymer is pure, it can have varying surface configurations. The polymer surface may not be homogeneous, or coatings, if any, may not be uniformly applied, or the surface, itself may have developed cracks, all of which can contribute to the incompatibility of the surface with the body.

With some degree of success, polyethylene glycol (PEG) has been used to coat polymeric surfaces in order to repel proteins from the surface after implantation. Similarly, heparin has been either covalently bound or ionically bound to polymeric surfaces in order to prevent blood coagulation thereabout after implantation. However, ionically bound heparin is gradually released from the implant surface providing only short-term anticoagulant effect, and covalently bound heparin, while remaining bound to the surface for longer periods of time, is not as effective an anticoagulant. Thus, where the object to be implanted is intended to remain for a long period of time, the anticoagulant of choice is covalently bound heparin.

While finding solutions to the problem of biocompatibility can be quite difficult, since proper operation of the sensor requires that certain membranes be in contact with the patient's blood, still what is needed are membranes that are biocompatible yet maintain their functionality or that may be treated, for example by application of an appropriate coating, to possess these characteristics. Additionally, an enzyme-based glucose monitoring system designed to protect against the problem of oxygen deficit while providing quick, accurate and continuous glucose concentration readings over a long term is desirable.

SUMMARY OF THE INVENTION

The subject matter described and claimed herein advantageously addresses these and other needs by providing an implantable monitoring system, particularly an implantable enzyme-based monitoring system, having improved biocompatibility and, therefore, sensor longevity while maintaining and even further improving the sensor's reliability, accuracy, and responsiveness to measuring the concentration of one or more prescribed substances, such as glucose, within a patient's blood. In particular, the monitoring system described herein employs improved configurations and provides for specialized treatment of the exterior surfaces of the implantable monitoring systems, which exterior surface treatment may be used in conjunction with almost any implantable monitoring system. The improved configurations include the use of a window through which the substance of interest is able to diffuse into the system. The window optimizes blood access to the enzyme and/or sensor assembly, thereby improving the accuracy and responsiveness of the sensor assembly. Additionally, the improved configurations include a selectively permeable membrane cover for the window which, among other things, may be used to prevent unwanted substances from diffusing into the monitoring system, thereby improving the accuracy of the system, and/or to prevent the loss of enzyme and/or other substances from within the monitoring system. Additional advantages to such a window cover will be apparent to those of skill in the art. Further improvements described herein include tapered exterior surfaces proximate the window which permit uniform flow of blood over the window, thereby preventing stagnation of blood at or near the side windows; use of multiple sensor assemblies, preferably rotationally displaced with respect to one another, and non-linear overall configurations of the monitoring system, such as arcuate, spiral or helical configurations wherein the windows of the monitoring system are positioned within the interior facing surfaces of the non-linear configurations. Such additional modifications each improve the accuracy of the monitoring system by increasing the sample size and distribution and/or by preventing the body from interfering with access to the window within the system.

A still further important and advantageous feature of the preferred embodiment of the implantable monitoring system contemplated herein is a protective coating, and method of its application, which coating is placed on the exterior surface of all or selected portions of monitoring system in order to improve the biocompatibility of the monitoring system by preventing tissue growth and/or formation of blood clots on the assembly. The preferred coating materials include a combination of an anti-coagulant, to prevent or reduce blood clot formation on the sensor surface, and an anti-binding compound, to prevent or reduce protein binding (i.e. tissue growth) to the sensor surface. In a particularly preferred embodiment, use of heparin in combination with polyethylene glycol (PEG) to achieve this improved biocompatibility is described.

These and other objects, features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

In the following detailed description, reference will be made to the attached drawings in which.

DETAILED DESCRIPTION OF THE PREFERRED EMBODIMENTS

Figure 1:
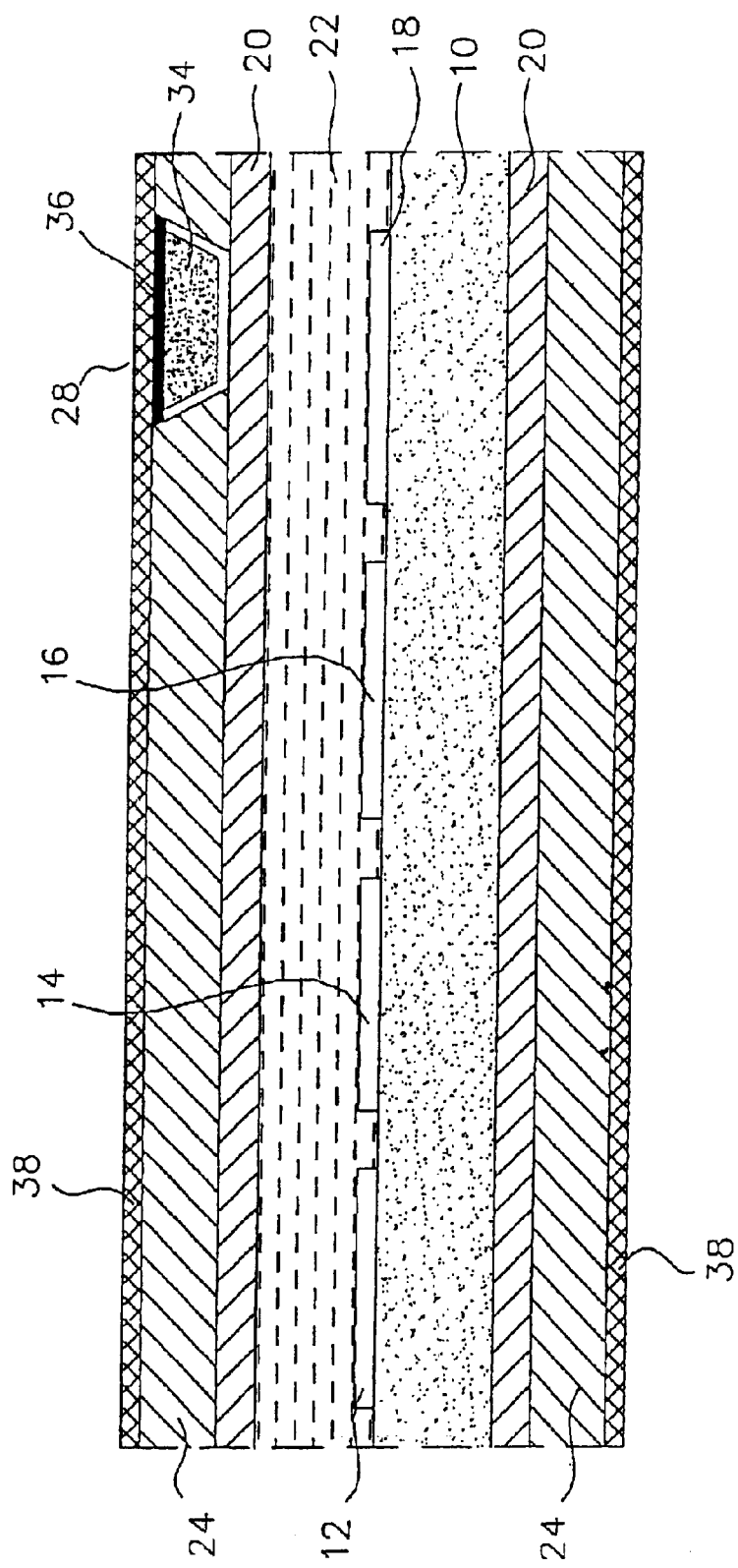
FIG. 1 is a cut away side view of a portion of a preferred embodiment of an implantable, enzyme-based glucose monitoring system, generally showing one embodiment of the sensor assembly thereof and specifically illustrating the polymeric window cover and exterior surface coating as disclosed herein.

The following description is of the best mode presently contemplated for carrying out the invention. For example, a preferred embodiment described herein is directed to an implantable enzyme-based glucose monitoring system. It will be appreciated by those of skill in the art that the improvements described herein may be used for implantable monitoring systems other than those that are enzyme-based and/or other than those designed to measure glucose concentrations. Thus, this description is not to be taken in a limiting sense, but is made merely for the purpose of describing the general principles of the invention. The scope of the invention should be determined with reference to the claims.

The numbering between Figures is consistent, such that the same item illustrated in more than one Figure bears the same identifying number in each Figure.

Definitions

As used herein, the term sensor assembly refers to that portion of the monitoring system that is directly involved in sensing the concentration of the substance(s) being measured, that is the substrate and associated electronics, membranes, enzyme(s) and solutions. An enzyme-based monitoring system, as contemplated herein, may, and preferably does, include more than one sensor assembly. In each of FIGS. 1 and 2, a single sensor assembly is illustrated within the outer membrane of the monitoring system. Thus, the outer membrane (and window therein), window cover and exterior surface coating are not encompassed by the term "sensor assembly" as used herein.

As used herein, the term implantable monitoring system refers to the whole implantable device. Thus, an implantable monitoring system (or simply, monitoring system) includes at least one sensor assembly housed within an outer membrane. In the most preferred embodiments the monitoring system has more than one sensor assembly and the outer membrane has at least one window associated with each sensor assembly, which window is covered by a window cover and which outer membrane and window cover are coated with a coating to resist blood coagulation and protein binding thereto.

It is noted that the term biocompatible, as used herein, refers to non-toxicity. As is readily apparent to those of skill in the art, it is important that the materials used to manufacture the monitoring system, at least to the degree they come in contact with the patient's body, not be toxic to the patient into whom the system is implanted. Thus, for example, any coatings added to the exterior surface of the monitoring system should be non-toxic to the patient as well as be able to withstand the stresses of constant blood flow there-across.

It is also noted that the coatings described herein are designed to resist and/or prevent thrombosis and/or tissue growth at the surface of the implanted monitoring system. Thus, reference to the "anti-coagulation" properties of the coating are synonymous with the anti-thrombosis properties thereof, and reference to the "anti-encapsulation" properties of the coating are synonymous with the anti-tissue growth properties thereof. In a preferred embodiment, the primary characteristic of the coating that provides anti-tissue growth properties is the ability of the coating to prevent/resist protein binding thereto. However, coatings capable of preventing tissue growth about the exterior surface of the monitoring system through other means are likewise contemplated herein. Thus, it is the function of the coating, to resist and/or prevent blood coagulation and/or to prevent tissue growth, that is most important to the present invention.

Description

Figure 2:
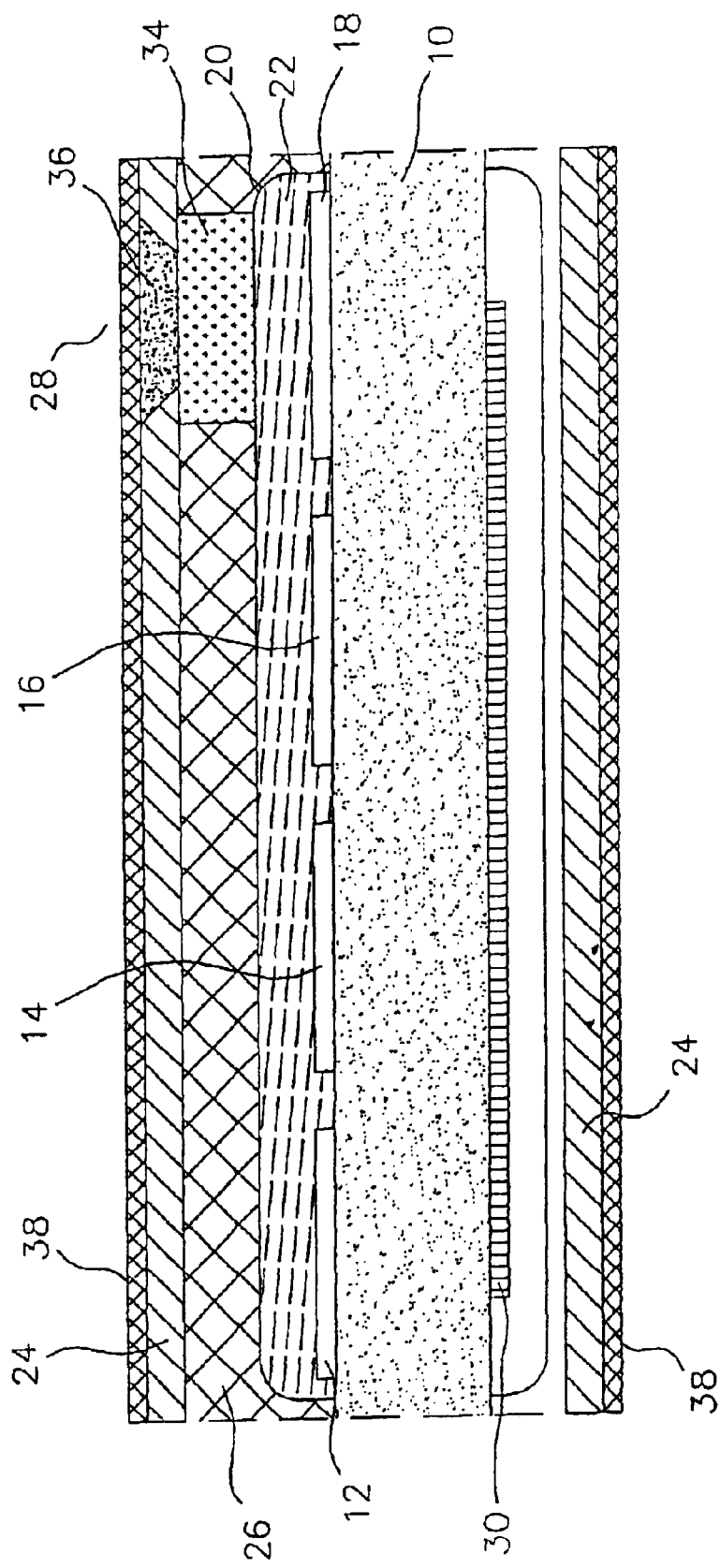
FIG. 2 is a cut away side view of a portion of a preferred embodiment of an implantable enzyme-based glucose monitoring system, generally showing an alternative embodiment of the sensor assembly thereof and specifically illustrating the polymeric window cover and exterior surface coating as disclosed herein.

FIGS. 1 and 2 illustrate the portion of two alternative implantable glucose monitoring systems wherein a sensor assembly is located. Each of these illustrated monitoring systems show preferred embodiments of the window, window covering and exterior coating as described and claimed herein. The alternative sensor assembly configurations are illustrative of specific examples of improved implantable monitoring systems as herein described.

In preferred embodiments, the monitoring system includes more than one sensor assembly. The sensor assemblies are preferably strung together in a daisy chain fashion, for example as is detailed in U.S. patent application Ser. No. 08/928,867, now U.S. Pat. No. 5,999,848 Gord, et al., "Daisy-Chainable Sensors and Stimulators for Implantation in Living Tissue", filed Sep. 12, 1997, which is incorporated herein in its entirety. Such a multi-sensor monitoring system advantageously permits multiple, simultaneous and/or contemporaneous concentration readings which thereby significantly increase the accuracy of the monitoring system. In order to further improve the accuracy of the preferred, multi-sensor monitoring system, and as described further below, the sensor assemblies are rotationally displaced relative to one another resulting in differing orientations within the patient's body and thus an increased variation in the sampling.

For detailed discussions of the systems contemplated for use with the subject matter described herein, especially those designed for monitoring in vivo glucose concentrations see, for example, U.S. patent application Ser. No. 08/444,300, now U.S. Pat. No. 5,660,163 Schulman, et al., entitled "Glucose Sensor Assembly"; U.S. Pat. No. 5,497,772, Schulman, et al. and U.S. patent application Ser. No. 08/953,817, now U.S. Pat. No. 6,081,736, filed Oct. 20, 1997, Schulman, et al., "Implantable Enzyme-Based Monitoring Systems Adapted for Long Term Use" filed Oct. 20, 1997, each of which patent applications and patents is hereby incorporated, by reference, in its entirety.

FIGS. 1 and 2 each illustrate a portion of a monitoring system having the polymeric window covering and exterior surface coating as contemplated herein. These figures also show, in a general manner, alternative sensor assembly configurations that may be used within the monitoring system. The primary difference between the two sensor assemblies illustrated in FIGS. 1 and 2 is the location of the microprocessor and associated microelectronics on the same substrate as the electrodes, as illustrated in FIG. 2, or elsewhere, as in FIG. 1. With respect to FIG. 1, the microprocessor and microelectronics are preferably located outside the patient's body as described, for example, in U.S. Pat. No. 5,660,163, issued to Schulman, et al. on Aug. 26, 1997, hereby incorporated by reference in its entirety.

Turning then to FIG. 1, illustrated is a substrate 10 having four electrodes, a first working electrode 12, a reference electrode 14, a counter electrode 16 and a second working electrode 18, affixed thereto. Preferably, the two working electrodes 12 and 18 are most distant each other on the substrate; whereas the reference 14 and counter 16 electrodes are located in any convenient position. Surrounding the electrodes, and forming a chamber thereabout, is a first membrane 20 that is selectively permeable. In preferred embodiments this first membrane 20 is hydrophobic and oxygen permeable. An electrolyte solution 22 is contained within the chamber and bathes the electrodes therein. Adjacent the first membrane 20 is an outer membrane 24 that also is selectively permeable. Again, in preferred embodiments, the outer membrane 24 is oxygen permeable and hydrophobic. It is this outer membrane 24 that comes in direct contact with the patient's body upon implantation and thus must be biocompatible.

A window or pocket 28 is formed within the outer membrane 24 at a point adjacent the second working electrode 18. Preferably, the window is formed with smooth, tapered surfaces or edges, thereby maintaining a controlled, uniform flow of blood over the window while preventing any stagnation of blood near the window and thereby minimizing the formation of blood clots. In this preferred embodiment, an enzyme solution 34 is contained within the window/pocket 28. The enzyme solution may be gelatinous, such as is described by Gough in U.S. Pat. No. 4,890,620, incorporated herein in its entirety, or it may be a fluid solution, such as that described in U.S. patent application Ser. No.08/953,817, now U.S. Pat. No. 6,081,736 filed Oct. 20, 1997, Schulman, et al., "Implantable Enzyme-Based Monitoring Systems Adapted for Long Term Use", incorporated by reference, above. Additionally, it is noted that the window 28 may be either a hole completely through the outer membrane 24 or a pocket within the outer membrane which is open to the exterior of the monitoring system.

A polymeric cover 36 covers the opening of the window or pocket. The cover 36 is preferably biocompatible, permeable to oxygen and glucose, has a mechanical strength comparable to that of the outer membrane 24 and adheres well to the material used to form the outer membrane 24. This cover serves the dual purpose of preventing unwanted substances from entering the monitoring system and thereby possibly contaminating the sensor assembly or interfering with its operation and of keeping in the enzyme solution 34 and/or other reagents contained within the monitoring system.

The window cover 36 is associated with the outer membrane 24. This may be accomplished by adhering the window cover 36 to the exterior surface of the outer membrane 24 near the edge of the window 28, as illustrated in FIG. 1, or it may be accomplished by forming the window cover 36 within the window 28, as illustrated in FIG. 2. Where the latter positioning is used, the window cover is adhered to the inner edge of the window 28, which inner edge is preferably tapered, as previously described. It is noted that adherence of the window cover 36 to the outer membrane 24 may be accomplished in a number of ways. What is critical is that the adherence be such that the window cover 36 remains in place despite the constant flow of blood there-across.

Additionally, in this preferred embodiment, some or all of the exterior surface of the monitoring system has an exterior coating applied thereto that includes an anti-coagulant and/or anti-tissue growth solution 38. Most preferably, this exterior coating is applied to the entire exterior surface of the monitoring system, including the exterior surface of the polymeric cover. Such a coating is advantageous both for improving the biocompatibility of the monitoring system and for preventing blood clotting and/or tissue growth in the area of the polymeric window cover. For example, if the edges of the window cover are rough or irregular, both blood clotting and tissue growth will be more likely to occur. Thus, application of the exterior coating in this area can reduce the likelihood of or prevent such problems, thereby increasing the in vivo longevity of the monitoring system.

Of course, it is not necessary to, and under certain circumstances may be advantageous not to, coat the entire exterior monitoring system with such an exterior coating. For example, the window cover may rest completely within the window/pocket opening and not extend above the tapered side-walls of the window/pocket. When this is so, the exterior coating may preferably be applied only to the exterior surface of the monitoring system and not to the window cover. Other such alternatives will be readily appreciable to those of skill in the art and are likewise contemplated herein. Both the polymeric window cover and exterior coating/treatment 38 of the outer membrane 24 are described in detail in the Examples that follow.

In operation of the monitoring system, oxygen diffuses into the system through both the outer membrane 24 and polymeric cover 36; whereas, glucose diffuses into the system only through the polymeric cover 36. Glucose and oxygen react in the presence of the enzyme 34 within the window/pocket 28 and the unreacted oxygen continues to diffuse through the system to contact the second working electrode 18. Simultaneously, oxygen diffuses into the monitoring system, in the areas where no enzyme is located, through to the first working electrode 12. Thus, the first working electrode 12 measures the background levels of oxygen and the second working electrode 18 measures the level of unreacted oxygen, thereby providing a determination of the in vivo glucose concentration.

As stated above, FIG. 2 illustrates an alternative embodiment of the sensor assembly employed in a glucose monitoring system according to the present invention. As with the sensor assembly of FIG. 1, this sensor assembly has a substrate 10 with four electrodes 12, 14, 16 and 18 affixed thereto and a first membrane 20 that forms a chamber or pocket thereabout within which an electrolyte solution 22 is contained. In this preferred embodiment, however, an intermediate membrane 26 is added between the first membrane 20 and outer membrane 24. This intermediate membrane 24 is preferably a hydrophobic, oxygen permeable membrane and is positioned adjacent the first working 12, reference 14 and counter 16 electrodes, only. The intermediate membrane 26 is not adjacent the second working electrode 18, rather, the intermediate membrane 26 helps to form a chamber adjacent the second working electrode 18 within which the enzyme solution 34 is contained.

Also illustrated in this alternative embodiment, is a microelectronics assembly 30 affixed to the substrate 10 on the side opposite the electrodes 12, 14, 16 and 18. A lid 32 covers the microelectronics assembly 30 and is affixed to the substrate 10 so as to provide a hermetic seal therewith. The details of this particular sensor assembly embodiment, are in U.S. patent application Ser. No. 08/953,817, now U.S. Pat. No. 6,081,736, filed Oct. 20, 1997, entitled "Implantable Monitoring Systems-Adapted for Long Term Use In vivo," filed simultaneously herewith. This application is incorporated, in its entirety, by reference herein.

As with the system illustrated in FIG. 1, that of FIG. 2 has an outer membrane 24, surrounding the interior workings just described. A window 28 is formed in the outer membrane 24 at a point adjacent the second working electrode 18, as described with respect to FIG. 1. It is noted that the window 28 of this embodiment is necessarily a hole through the outer membrane 24 and is not a pocket. Covering the window 28 opening, is a polymeric cover 36 as described above and detailed in the Examples below. The outer membrane is constructed of a hydrophobic and oxygen permeable material, such as silicon rubber, and an exterior coating is applied to reduce and/or prevent blood coagulation and tissue formation thereon. Such exterior coating is also detailed in the Examples below.

Thus, the embodiment depicted in FIG. 2 operates in generally the same manner as that described for the FIG. 1 embodiment. For a detailed discussion of the configuration and operation of the monitoring systems generally illustrated herein, see U.S. Pat. No. 5,497,772, Schulman, et al.; U.S. Pat. No. 4,890,620, Gough, et al.; and U.S. patent application Ser. No. 08/953,817, now U.S. Pat. No. 6,081,736 filed Oct. 20, 1997, Schulman, et al., each of which have been previously referred to and incorporated in their entirety herein.

Turning to the Examples, described are the materials and methods for carrying out preferred embodiments of the present invention. Alternative materials that function in substantially the same manner will be evident to those of skill in the art and are likewise contemplated herein.

EXAMPLE 1

Polymeric Window Cover

As stated above, the materials of the polymeric cover for the window in the outer membrane of the preferred, glucose monitoring system must be chosen to be biocompatible, glucose and oxygen permeable and have a mechanical strength comparable to, and be able to adhere well to, the outer membrane. In preferred embodiments, the outer membrane is formed of silicone rubber, thus it is this material to which the polymeric window cover must adhere and comparable to which the cover's mechanical strength should be.

Preferable herein, is a polymeric system of 2-hydroxyethyl methacrylate (HEMA), N,N,-dimethylaminoethyl methacrylate (DMAEMA) and methacrylic acid (MA) in weight ratios of 50:25:25. Following is a preferred method of preparing this co-polymer.

Preparation of Polymeric Window Covering

To a 20 ml scintillation vial the following purified components are added then well agitated:

| | |
|---|---|
| 2-Hydroxyethyl methacrylate | 0.50 g (±0.01 g) |
| Methacrylic acid | 0.25 g (±0.005 g) |
| Dimethylamino ethyl methacrylate | 0.25 g (±0.005 g) |
| Ethylene glycol | 1.0 g (±0.05 g) |
| Ethylene glycol dimethacrylate | 0.1 g (±0.005 g) |
| Camphoquinone | 3.5 mg (±0.1 mg) |
| Escolol 507 | 5.0 mg (±0.1 mg) |

Once mixed by agitation, the window covering is stored at room temperature in the absence of light. When ready to be used, the window covering is applied to the window using a syringe and photo-polymerized in situ.

EXAMPLE 2

Surface Modification of Exterior of Monitoring System

Modification of the silicone exterior of the monitoring system to improve the longevity of the system by making it more resistant to blood coagulation and tissue growth was accomplished by first, etching the surface of the silicone; then introducing amino groups on to the etched silicone surface; next, simultaneously, covalently grafting heparin and polyethylene glycol (PEG) to the surface; and finally, ionically binding additional heparin to the surface. In a preferred embodiment the final molar ratio of heparin to PEG is 20 to 80, as described further, below.

Once completed, the resulting monitoring system has the advantage of powerful, short-term anti-coagulation protection, provided by the ionically bound heparin, which slowly dissipates over time as the ionic bonds break and the heparin leaches from the system; and the system has stable long-term anti-coagulant protection from the covalently bound heparin. The covalently bound PEG operates to minimize the protein deposition and fibrin sheath formation which is commonly observed on long-term implantable catheter surfaces, such as that of the monitoring system.

Plasma etching of the outer surface of the silicone outer membrane, in order to introduce hydroxyl groups thereto, was performed using standard methods. Amino groups were then introduced to the etched surface by reaction with functionalized silane. In order to achieve an efficient covalent grafting of heparin to the surface of the silicone, a water insoluble ionic complex of heparin with lipid molecules (Hep-L) was formed. Being soluble in many organic solvents, the complex was efficiently derivatized by tosylating one hydroxyl group per repeat unit of heparin. PEG was tosylated by standard methods, as known to those of skill in the art and the tosylated PEG and Hep-L complexes were subsequently reacted with the amino functionalized outer membrane exterior surface. Next, the lipid molecules were cleaved from the heparin by incubating the outer membrane with dilute HBr (pH=5), and finally, heparin was ionically bound to the exterior outer membrane surface, using standard techniques.

Figure 3:
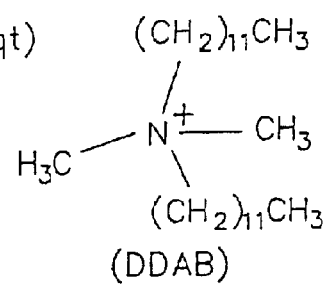
FIG. 3 is a schematic of the preferred derivatization of heparin described herein.
Figure 3:
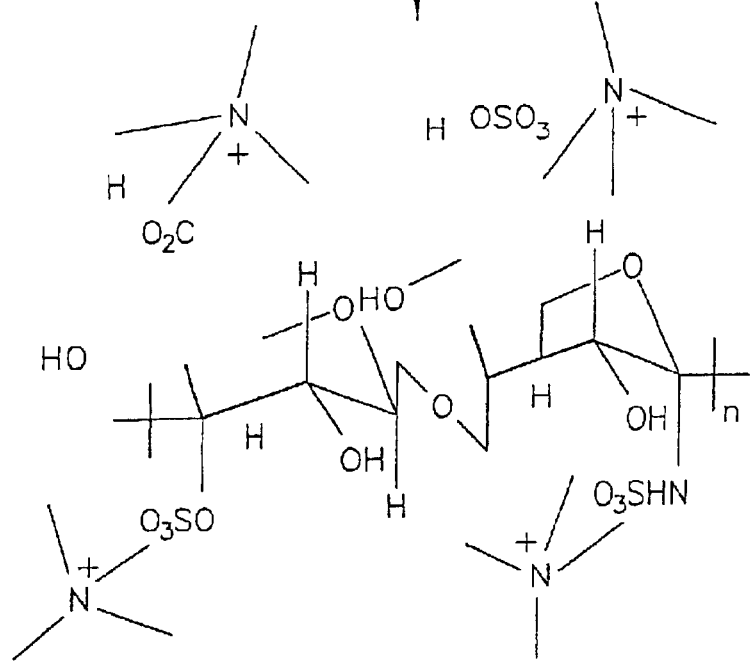
Figure 4:
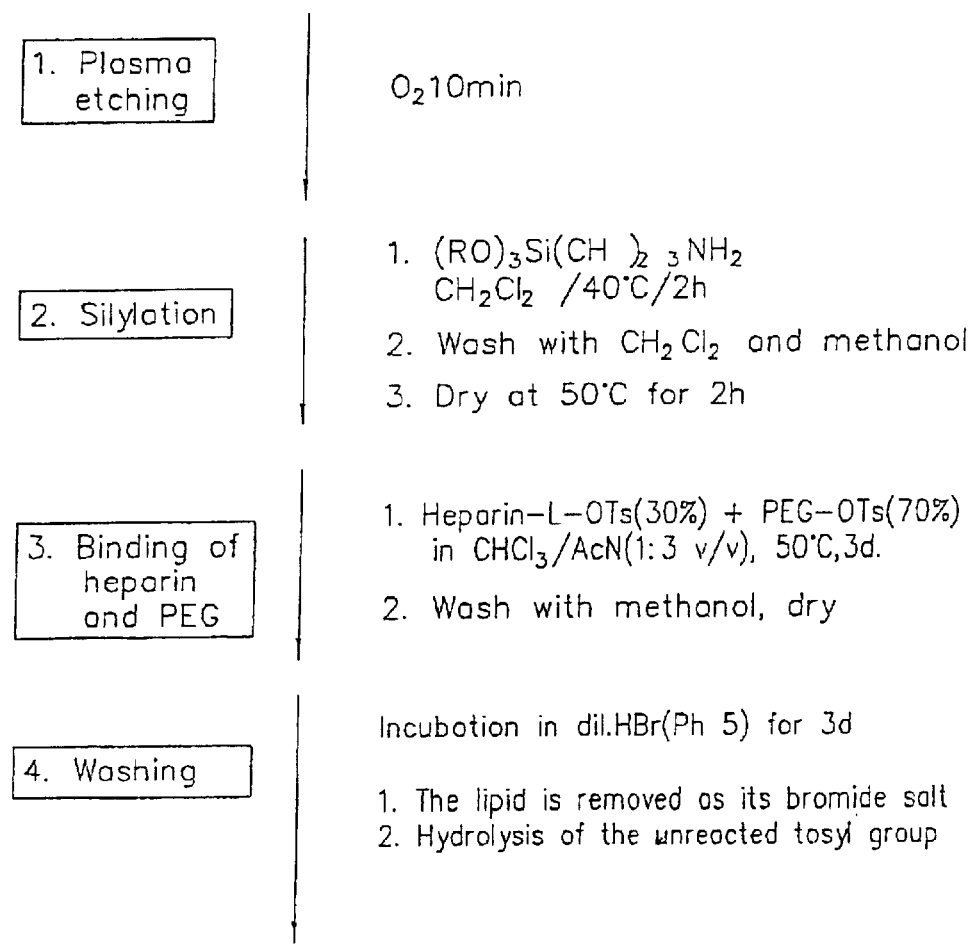
FIG. 4 is a schematic of the preferred process of covalent attachment of polyethylene glycol and heparin to the exterior surface of the monitoring system.
Figure 4:
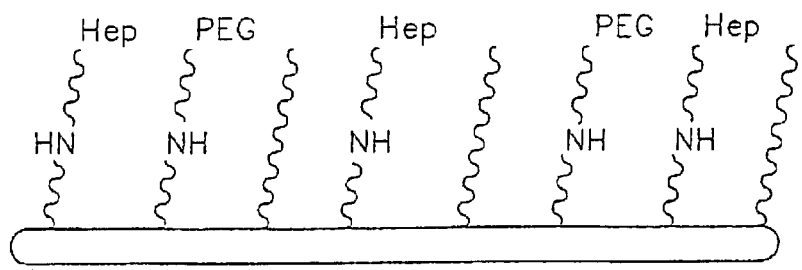
Figure 5:
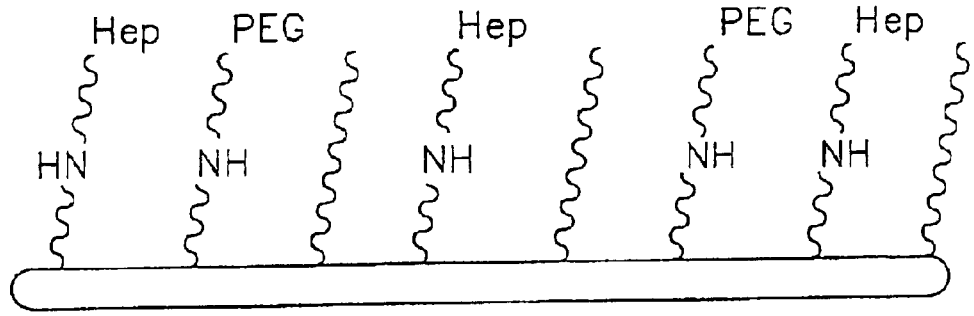
FIG. 5 is a schematic of the preferred process of ionic attachment of heparin to the monitoring system surface.
Figure 5:
Figure 5:
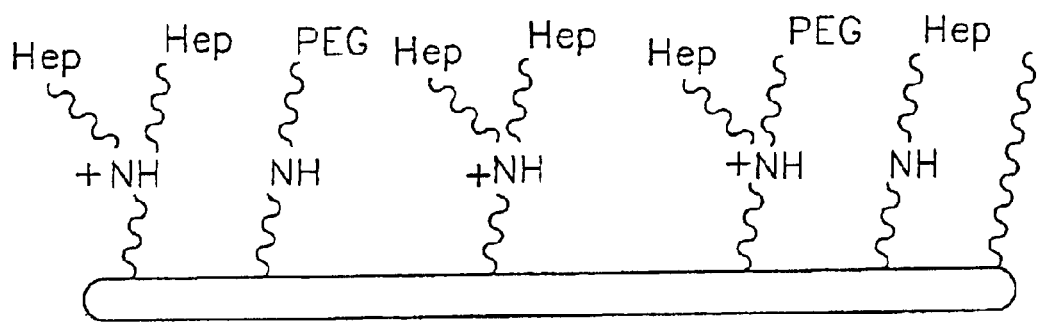

FIGS. 3, 4 and 5 illustrate these processes, schematically. FIG. 3 is a schematic of the derivatization of heparin. FIG. 4 is a schematic of the covalent grafting of heparin and PEG to the surface of the monitoring system, and FIG. 5 is a schematic of the ionic binding of heparin to that surface.

Figure 6:
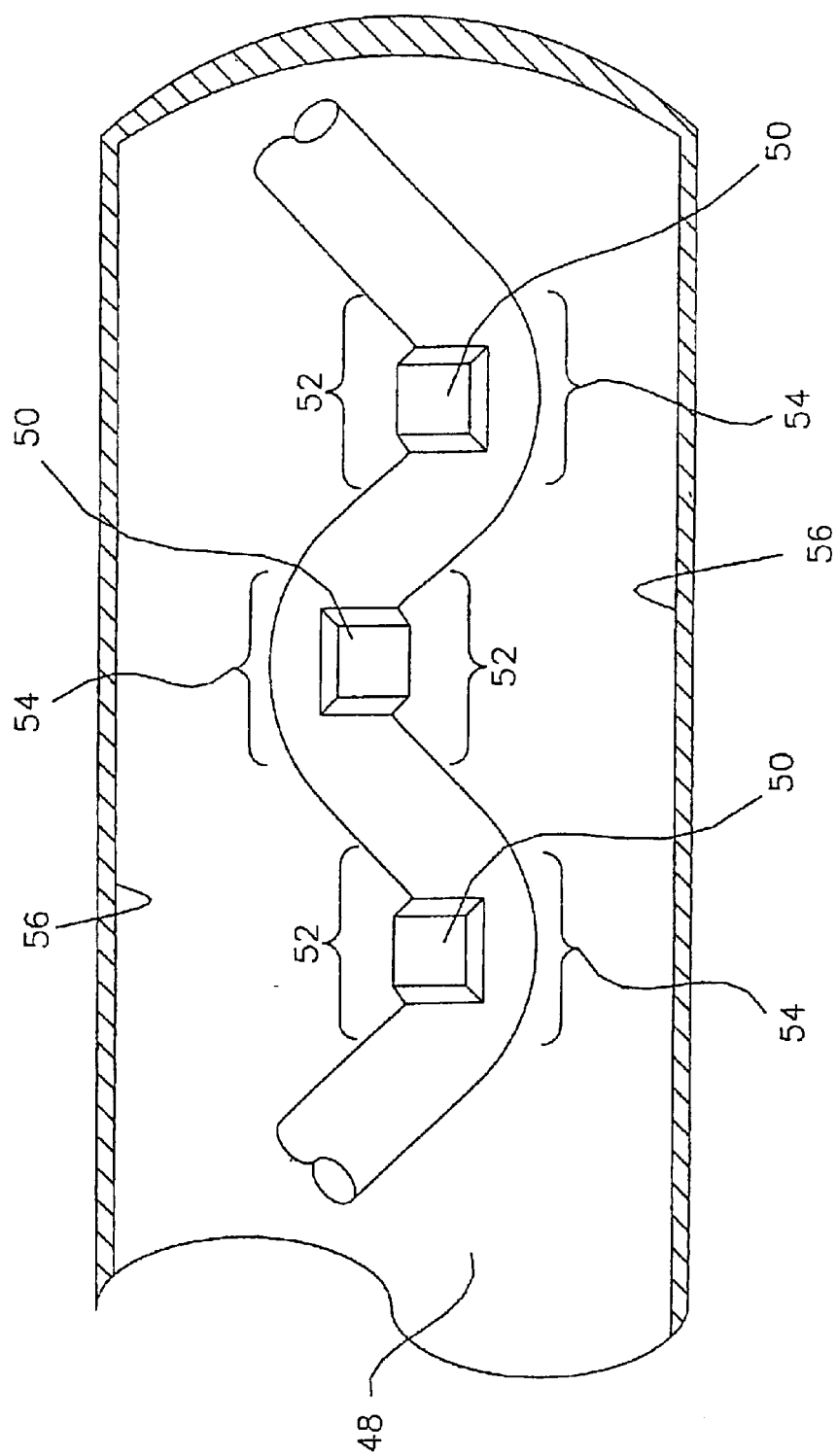
FIG. 6 is a partial view of an alternative embodiment of the implantable monitoring system placed in a blood vessel illustrating a non-linear configuration, that prevents the windows of the system from being situated against the blood vessel wall and blocking blood access thereto.

FIG. 6 illustrates a partial view of one embodiment of the preferred implantable monitoring system 48, having a non-linear configuration, as contemplated herein. Such non-linear configurations are particularly advantageous in that they prevent the sensing elements from being or becoming placed or oriented against the blood vessel wall 56. Placement of the monitoring system against the blood vessel promotes stagnation of the blood and limits the accuracy of glucose level measurements because the window(s) and underlying glucose sensing elements are not continually exposed to free flowing blood. By adding curves to the overall monitoring system configuration, it can, at most, contact the walls of the blood vessel in only small areas rather than along its full length. It is noted that it may be necessary to also modify the shape of the sensor assembly substrate, for example to also be arcuate.

Thus, FIG. 6 illustrates a portion of an implantable monitoring system, as contemplated herein, wherein the shape has an arcuate configuration, with the windows 50 placed on the interior facing surface of the arcs 52. The exterior facing surfaces 54 of the arcs are, then, necessarily situated closer to the blood vessel wall 56. This specially designed configuration provides uniform and consistent blood flow over the windows of the monitoring system. In this preferred embodiment, three glucose sensor assemblies are present, as illustrated by the three windows 50 which are adjacent each sensor assembly. It will be appreciated by those of skill in the art that various monitoring system configurations may be employed to achieve the same result as is achieved by the S-shape shown in FIG. 6. For example, a spiral shape may be used, wherein the windows of the monitoring system are preferably positioned on the interior face of the spiral. Similarly, more than one sensor assembly may be positioned along the interior face of a single arc/curve in the monitoring system configuration. Such alternatives are equally contemplated herein.

Figure 7:
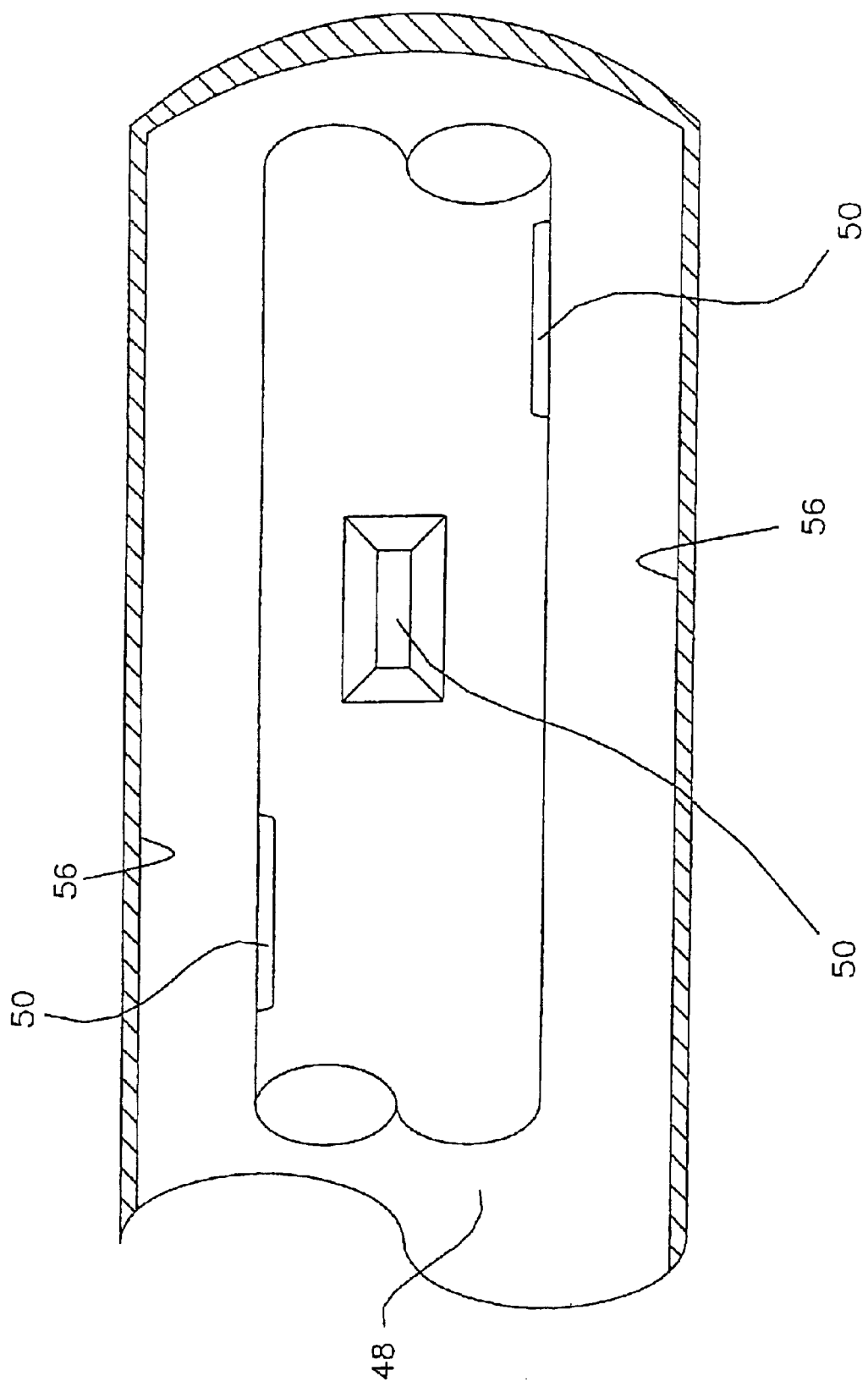
FIG. 7 is a partial view of an alternative embodiment of the implantable monitoring system having the multiple sensor assemblies, as indicated by the multiple windows illustrated, which sensor assemblies (and therefore windows) are rotationally displaced with respect to one another.

FIG. 7 illustrates a partial view of yet another alternative embodiment of the implantable monitoring system as contemplated herein. In particular, FIG. 7 shows an alternative configuration that, like the configuration shown in FIG. 6, improves the overall accuracy of the monitoring system by reducing the likelihood that all, or a significant portion of, the sensing elements could be placed or oriented against the blood vessel wall 56. In this embodiment, the windows 50 on the outer membrane of the monitoring system are rotationally displaced, with respect to one another, around the circumference of the monitoring system. The sensor assemblies (not shown) within the monitoring system, therefore, are also rotationally displaced with respect to one another and in alignment with the windows. As can be seen in FIG. 7, should the monitoring system come to rest against the vessel wall, only a limited number of the windows (and therefore, sensors) will be blocked thereby. Alternative configurations and combinations will be apparent to those of skill in the art and are likewise contemplated herein. Additionally, it is noted that the monitoring system illustrated in FIG. 6 also requires the sensor assemblies to be rotationally displaces with respect to one another. The particular embodiment illustrated in FIG. 6, would have the sensor assemblies rotationally displaced at 180° from one another.

From the foregoing, it should be appreciated that the present invention thus provides an implantable enzyme-based monitoring system adapted for the continuous in vivo measurement of bio-chemicals, such as glucose over an extended period of time. Further, it will be apparent that various changes may be made in the form, construction and arrangement of the parts thereof without departing from the spirit and scope of the invention or sacrificing all of its material advantages, the forms hereinbefore described being merely exemplary embodiments thereof.

To that end, it is not intended that the scope of the invention be limited to the specific embodiments and processes illustrated and described. Rather, it is intended that the scope of this invention be determined by the appending claims and their equivalents.

What is claimed is:

1. An implantable monitoring system comprising:
   a plurality of sensor assemblies coupled in a daisy chain, each sensor assembly having a sensing area for sensing a parameter of an implant environment; and
   a membrane for housing the plurality of sensor assemblies;
   wherein the configuration of the monitoring system is non-linear.

2. An implantable monitoring system according to claim 1, wherein at least three sensing areas are facing three distinct directions.

3. An implantable monitoring system according to claim 1, wherein at least two sensing areas are rotationally displaced approximately 180 degrees relative to a longitudinal dimension of the membrane.

4. An implantable monitoring system according to claim 1, wherein the membrane is curved along a longitudinal dimension of the membrane.

5. An implantable monitoring system according to claim 4, wherein each sensing area is located on a concave portion of the membrane.

6. An implantable monitoring system according to claim 5, wherein the membrane is spiral along the longitudinal dimension of the membrane.

7. An implantable monitoring system according to claim 5, wherein the membrane is acruate along the longitudinal dimension of the membrane.

8. An implantable monitoring system according to claim 5, wherein the membrane is S-shaped along the longitudinal dimension of the membrane.

9. An implantable monitoring system comprising:
   a plurality of sensor assemblies coupled in a daisy chain, each sensor assembly having a sensing area for sensing a parameter of an implant environment;
   a membrane for housing the plurality of sensor assemblies;
   wherein the membrane is curved along a longitudinal dimension; and
   wherein the sensor assemblies are disposed along the longitudinal dimension of the membrane.

10. An implantable monitoring system to claim 9, wherein each sensing area is located on a concave portion of the membrane.

11. An implantable monitoring system according to claim 10, wherein the membrane is spiral along the longitudinal dimension of the membrane.

12. An implantable monitoring system according to claim 10, wherein the membrane is arcuate along the longitudinal dimension of the membrane.

13. An implantable monitoring system according to claim 10, wherein the membrane is S-shaped along the longitudinal dimension of the membrane.

* * * * *